United States Patent [19]

Oppenheimer et al.

[11] 4,146,628

[45] Mar. 27, 1979

[54] ANTIARRHYTHMIC QUINUCLIDINE CARBOXYLIC ACID XYLIDIDE AND METHOD OF PRODUCING THE SAME AND SIMILAR COMPOUNDS

[76] Inventors: Edna Oppenheimer, No. 6, Horkanus St., Tel Aviv; Eliezer Kaplinsky, 21 Emek Dotan St., Tel Hashomer; Sasson Cohen, 10 Meyzan St., Tel Aviv, all of Israel

[21] Appl. No.: 821,748

[22] Filed: Aug. 4, 1977

[51] Int. Cl.$^2$ ............................................. A61K 31/445
[52] U.S. Cl. ..................................................... 424/267
[58] Field of Search ......................................... 424/267

[56] References Cited

FOREIGN PATENT DOCUMENTS 1566045  3/1969  France.

*Primary Examiner*—Donald B. Moyer
*Attorney, Agent, or Firm*—Harold D. Steinberg; Alfred Halpern

[57] ABSTRACT

The invention relates to the compound 2-6-xylidide of quinuclidine-3-carboxylic acid and its pharmaceutically acceptable salts, such as the hydrochloride, which have been found to be effective antiarrhythmic agents. The invention further relates to the production of this antiarrhythmic compound which method is applicable also to the production of related compounds which, however, do not have antiarrhythmic action, e.g. the quinuclidine-2-carboxylic acid xylidides. The compounds are produced according to this method by reacting the quinuclidine carboxylic acid in anhydrous chloroform and oxalyl chloride with the dimethylaniline. The desired compound is produced in high yield with a high degree of purity.

5 Claims, No Drawings

ANTIARRHYTHMIC QUINUCLIDINE CARBOXYLIC ACID XYLIDIDE AND METHOD OF PRODUCING THE SAME AND SIMILAR COMPOUNDS

BACKGROUND OF THE INVENTION

Lidocaine and similar compounds have been used for the treatment of cardiac arrhythmias, however, while the same are used in coronary intensive care units, it cannot be used in the prophylaxis of the sudden death syndrome because its biological half life is only about 75 minutes. Furthermore, the absorption of lidocaine from the intestinal tract is unsatisfactory and this substance provides undesirable side effects such as hypotension, neurotoxicity and low therapeutic index. Still further, due to the rapid metabolism thereof, the lidocaine must be administered by continuous intravenous infusion in order to maintain adequate plasma concentrations.

Consequently, there has been continuous research in the field to try to provide agents with improved antiarrhythmic action.

French Pat. No. 1,566,045 to Aktiebolaget Astra describes the general group of compounds of the formula:

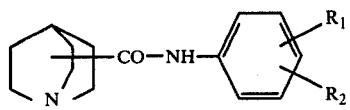

wherein $R_1$ and $R_2$ are hydrogen, halogen or loweralkyl. The patent also describes the production of these compounds by converting the quinuclidine carboxylic acid to its methyl ester followed by treatment with a mixture of methylmagnesium iodide and the selected aniline. However, yields are low and are contaminated with undesired side products.

The French patent specifically discloses the 2,6,-xylidide of quinuclidine-2-carboxylic acid and the compound is indicated as having antiarrhythmic and local anaesthetic action. However, our tests have proved that this compound is neurotoxic and is completely devoid of any useful antiarrhythmic action.

The article of Dahlbom and Dolby in Acta Pharma. Suecica 65. 277 (1969) describes various derivatives of quinuclidine-3-carboxylic acid including the compound N-(quinuclidine-3-carbonyl)-2,6-dimethylaniline, which compounds were tested for various pharmacological and microbiological activities and were found to have no pharmacological effect except for a weak local anaesthetic action.

The compounds are produced according to the article in Acta Pharm. Suecica by reacticing the quinuclidine carboxylic acid hydrochloride with the aniline e.g. 2,6-dimethylaniline under refluxing in the presence of thionyl chloride. However, this reaction causes extensive discoloration of the reaction mixture and in the formation of sulfur-containing material of unknown composition which contaminates the desired product. The yield of partially purified product by this procedure can rarely exceed 60% of the theoretical.

SUMMARY OF THE INVENTION

Generally speaking it has been found in accordance with the present invention that contrary to the teaching in Acta Pharm. Suecica the 2,6-xylidide of quinuclidine-3-carboxylic acid, and the pharmaceutically acceptable salts thereof such as the hydrochloride, have a highly pronounced cardiac antiarrhythmic action without undesirable side effects, which is most surprising in view of the fact that comparative tests have shown that the 2,6-xylidide of quinuclidine-2-carboxylic acid of French Pat. No. 1,566,045 is neurotoxic and devoid of any useful cardiac antiarrhythmic effect.

The invention further relates in general to the production of quinuclidine carboxylic acid and aniline derivatives of the formula:

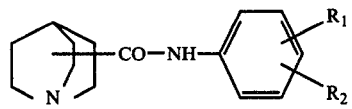

wherein $R_1$ and $R_2$ are hydrogen, halogen or lower alkyl by reacting the quinuclidine carboxylic acid in anhydrous chloroform in the presence of oxalyl chloride with the selected aniline derivative. This method results in the production of the desired compound in pure form in yields of 90% or more of the theoretical.

It is accordingly a primary object of the present invention to provide new and effective cardiac antiarrhythmic compositions.

It is yet a further object of the present invention to provide for the treatment of cardiac arrhythmia utilizing the cardiac antiarrhythmic compositions of the present invention.

It is yet a further object of the present invention to provide a general method of producing aniline derivatives of quinuclidine carboxylic acids and specifically of producing the antiarrhythmic 2,6-xylidide of quinuclidine-3-carboxylic acid.

Other objects and advantages of the present invention will be apparent from a further reading of the specification and of the appended claims.

With the above and other objects in view, the present invention mainly comprises as a cardiac antiarrhythmic pharmaceutical composition a pharmaceutical carrier and a cardiac antiarrhythmic effective amount of the 2,6-xylidide of quinuclidine-3-carboxylic acid or a physiologically acceptable salt thereof.

The present invention further comprises the method of producing 2,6-xylidide of quinuclidine-3-carboxylic acid and of related compounds by reacting the quinuclidine carboxylic acid (or its acid addition salt, e.g. the hydrochloride) in anhydrous chloroform in the presence of oxalyl chloride with the selected aniline, under refluxing.

As indicated above, it has been found according to the present invention that while the 2,6-xylidide of quinuclidine-2-carboxylic acid is neurotoxic and devoid of useful cardiac antiarrhythmic action, the isomer thereof, namely 2,6-xylidide of quinuclidine-3-carboxylic acid of the formula:

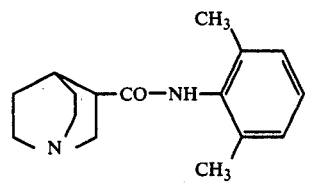

exhibits pronounced cardiac antiarrhythmic activity with a minimum of side effects. In effecting cardiac antiarrhythmic action it is preferred to utilize a cardiac antiarrhythmic effective amount of the hydrochloride of the 2,6-xylidide of quinuclidine-3-carboxylic acid although it is possible to use any physiologically acceptable salt thereof. The hydrochloride is both highly soluble and easily obtainable and is therefore most preferred.

In establishing the effective cardiac antiarrhythmic action of the present invention, the hydrochloride of 2,6-xylidide of quinuclidine-3-carboxylic acid (hereinafter referred to for convenience as "Compound I") was compared with previously known cardiac antiarrhythmic agents for evaluation, and was also compared with the hydrochloride of 2,6-xylidide of quinuclidine-2-carboxylic acid (hereinafter referred to as "Compound II").

DESCRIPTION OF PREFERRED EMBODIMENTS

The following examples are given to illustrate the method of the present invention. However, the invention is not meant to be limited to the specific details of the examples.

EXAMPLE 1

This example illustrates the production of 2,6-xylidide of quinuclidine-3-carboxylic acid hydrochloride (Compound I) utilizing the new method of the present invention.

2.5 g of quinuclidine-3-carboxylic acid hydrochloride (0.013 mole) was dissolved in anhydrous and alcohol-free chloroform (150 cc). Oxalyl chloride (10 ml) was added and the mixture was refluxed for 3 hours in a glass assembly protected from atmospheric moisture. The solvents were evaporated off to dryness.

Following this, the mixture was treated with a solution of 3 g (0.025 mole of 2,6-dimethylaniline in 100 ml anhydrous, alcohol-free chloroform and refluxed for 6 hours. All volatile solvents were removed by distillation (oil bath at 80° C.) and the residue was treated with 25 ml of cold 3N aqueous hydrochloric acid.

The clear acid solution was decanted from a little insoluble residue and its pH was adjusted to 4.5 with 5% aqueous sodium hydroxide, it was extracted once with ether (25 ml) and the ether extract was discarded. The pH was raised to pH 8 and the aqueous solution was again extracted with 25 ml ether. The ether extract contained recovered 2,6-dimethylaniline. The aqueous solution was rendered strongly alkaline, whereupon the desired compound was obtained as a precipitate. This was extracted with 50 ml chloroform; the chloroformic solution was evaporated to dryness under reduced pressure, the residue was dissolved in 200 ml 5% methanolic hydrogen chloride and the resulting solution again evaporated to dryness. The residue was recrystallized from a mixture of methanol and ether (1:1). Yield: 3 g of the hydrochloride (Compound I) m.p. 234°–236°; a further quantity (0.5 g) was recovered from the mother liquor upon concentration. The combined yield of the pure compound was 91% of the theoretical.

Carrying out the above method, however, utilizing thionyl chloride in place of the oxyalyl chloride of the present invention results in extensive discoloration of the reaction mixture and formation of sulfur-containing materials of unknown composition which contaminate the desired product resulting in a yield of the partially purified product of not more than 60% of the theoretical.

EXAMPLE 2

This example illustrates the production of 2,6-xylidide of quinuclidine-2-carboxylic acid hydrochloride (Compound II) utilizing the method of the present invention.

1.5 g of quinuclidine-2-carboxylic acid hydrochloride (0.0078 mole) was dissolved in 100 ml anhydrous, alcohol-free chloroform. Oxalyl chloride (7 ml) was added and the clear mixture was refluxed for 3 hours in a glass assembly protected from atmospheric moisture, then the solvents were evaporated to dryness. The mixture was treated with a solution of 1.5 g (0.0125 mole) of 2,6-dimethylaniline in 50 ml anhydrous, alcohol-free chloroform and reflux resumed for 6 hours.

The volatile solvents were removed by distillation on an oil bath at 80° C. and the residue was dissolved in cold, 3N aqueous hydrochloric acid and decanted from a little insoluble residue. The clear solution was adjusted to pH 5.5 by the addition of 5% aqueous sodium hydroxide, then extracted with 25 ml ether. The ether extract contained recovered 2,6-dimethylaniline. The aqueous phase was made strongly alkaline with sodium hydroxide then extracted with 100 ml chloroform. The chloroformic extract was evaporated to dryness and the residue was layered on top of a column of chromatography grade neutral alumina of activity 1 and having the following dimensions: diameter, 2 cm; length, 50 cm. Impurities were flushed out first by eluting with about 1 liter benzene. The Compound II was then eluted with chloroform (500 cc). The chloroformic solution was evaporated to dryness and the residue was dissolved in 5% mathanolic hydrogen chloride (100 cc). Evaporation of this solution and recrystallization of the residue from a mixture of methanol + ether, 1:1, resulted in the hydrochloride (Compound II); yield 1 g (50% of theoretical), M.P. = 216° C.

The above method of producing Compound II is far superior to the method described in French Pat. No. 1,566,045 wherein quinuclidine-2-carboxylic acid is converted to its methyl ester which is treated with a mixture of methylmagnesium iodide and 2,6-dimethylaniline. The instant process produces a higher yield and greater purity. On the other hand, if it is attempted to produce Compound II utilizing thionyl chloride in place of oxalyl chloride as in the instant method, Compound II cannot be obtained in any measurable yield because of extensive decomposition of quinuclidine-2-carboxylic acid and the formation of sulfur-containing tarry products of unknown composition.

Evaluation of the antiarrhythmic action of Compound I, including evaluation of its other pharmacological characteristics and side effects, as compared to known antiarrhythmic agents, and also as compared to Compound II are detailed below.

The toxicity of Compound I was determined by i.p. injection of a 0.5% solution of the drug into male, albino ICR mice weighing 20–25 g each. A group of six mice was used for each dose. The $LD_{50}$ derived by probit analysis was found to be 60 ± 5 mg/kg.

The lack of interaction of Compound I with other centrally active drugs may also be taken as an indication of its lack of activity in the CNS. The following examples may be cited: Compound I did not affect metrazole-induced convulsions (metrazole, 100 mg/kg) when injected i.p. 30, 60 and 90 minutes prior to metrazole. It did not affect oxotremorine-induced tremors (oxotremorine, 20 μg/kg, i.p.) when given i.p. 30 minutes prior to oxotremorine. It was equally ineffective against Indoklon-induced seizures when the latter was administered 30 minutes later by inhalation, or electro shock-induced seizure, at a voltage of 30 volts.

Observations on conscious, healthy dogs that had received Compound I as a bolus intravanous injection over a period of 15–30 seconds and at a dose of 5 mg/kg revealed no significant change in posture, behavior or mood from control.

The effect of Compound I on the normal heart was determined by the administration of the compound as a bolus intravenous injection to conscious healthy dogs for which lead II of the electrocardiogram was monitored for as long as 2 hours after injection. In a total of 6 animals, a single dose of 3 mg/kg and a cumulative dose of 6 mg/kg, administered in divided doses of 3,2 and 1 mg/kg over a period of 30–60 minutes, elicited no change in the ECG.

In one case, a single dose of 5 mg/kg was administered rapidly in order to achieve a high but transient concentration in the heart. Broadening of the QRS complex was observed, but there were no other signs of overt toxicity in the animal. The ECG record reverted to normal within 15 minutes.

In one nembutal-anesthetized dog (nembutal, 25 mg/kg) a cumulative intravenous dose of 6 mg/kg, administered in divided doses of 3,2 and 1 mg/kg over a period of 30 minutes, elicited no change in the ECG.

Nembutal anesthetized cats responded differently. After a total dose of 3 mg/kg of Compound I given in small increments over 34 minutes, there was a leftward shift of the QRS complex. With a cumulative doses of 6 mg/kg, and 10.5 mg/kg broadening of the QRS occurred but sinus rhythm was maintained. At a still higher dose, e.g. 16.5 mg/kg (cumulative), second degree AV block occurred. Atrial conduction slowed down as seen from the widening of the P wave. If drug administration was discontinued at this stage, then the severe toxic effects would disappear after 40 minutes, the heart reverting to normal sinus rhythm. A further massive dose, e.g., 7.5 mg/kg (total cumulative dose: 23.5 mg/kg) resulted in a high degree AV block, followed by cardiac standstill.

The following describes tests which were carried out to determine the effect of ouabain-induced arrhythmias.

Cats of both sexes (1.8–3.4 kg) were anesthetized with nembutal (40 mg/kg, i.p.). The trachea was cannulated to insure a potent airway. Artificial respiration was used only when difficulties in respiration were observed after nembutal administration and before the administration of any other drug (2 cases out of 10). A femoral artery and vein were cannulated to record blood pressure and to administer drugs, respectively. Lead II of the electrocardiogram (ECG) was monitored throughout the experiment by means of a Grass Model 7 polygraph. All solutions were in saline. Arrhythmia was induced with oubain in two ways: either by injection of small doses of this drug every 30 minutes or by constant infusion. Usually, ventricular tachycardia (VT) set in after administration of a total dose of 75–80 μg/kg over a period of one hour at least.

After induction of arrhythmia, Compound I was administered as a bolus intravenous injection at a dose of 1 mg/0.2 ml/kg over a period of 30 seconds. In a number of cases, this treatment was repeated once, but at the reduced dose of 0.5 mg/kg this, if arrhythmia reappeared within one hour. For comparison, lidocaine was administered by the same procedure.

In other experiments using mongrel dogs, the animals were anesthetized by an i.v. injection of nembutal (25 mg/kg), then arrhythmia was induced by the administration of decreasing doses of ouabain at 30 minute intervals, 40, 20 and 10 μg/kg. Treatment with Compound I was then carried out as described for cats.

Ten minutes after the establishment of constant arrhythmia in cats with a cumulative dose of 70–90 μg/kg ouabain, administration of Compound I as a single therapeutic dose of 1 mg/kg resulted in a marked improvement of the ECG that lasted much longer than any improvement achieved with lidocaine used under identical conditions. The results for Compound I treated cats are given in Table 1 and those for lidocaine-treated cats are given in Table 2.

In dogs, reversal of VT to normal sinus shythm was achieved with 1 mg/kg single doses of Compound I. If arrhythmia reappeared after 45 minutes, reversal to normal sinus rhythm could be restored again with an additional dose of Compound I equal to half the initial dose (Table 3).

TABLE 1.

EFFECT OF COMPOUND I ON OUABAIN-INDUCED ARRHYTHMIA IN THE CAT

After anethesia with 40 mg/kg Nembutal, arrhythmia was induced by the administration of ouabain i.v., either in small doses or by constant infusion, to a total dose of 75–80 μg/kg. Then Compound I was given as a bolus i.v. injection of 1 mg/kg. (Nembutal was given i.p.)

| | Normal | | Arrhythmia | | | Compound I treated | | | |
|---|---|---|---|---|---|---|---|---|---|
| Serial | H.R. | B.P. | Type | H.R. | B.P. | S.R. | H.R. | B.P. | Duration (min) |
| 1 | 160 | 90/70 | VPB | 100 | 80/60 | + | 100 | 80/60 | 10[#] |
| 2 | 150 | 110/85 | VPB | 110 | 170/120 | + | 80 | 110/90 | 75[##] |
| 3 | 140 | 130/80 | VPB | 140 | 120/100 | + | 110 | 130/90 | 4 hrs. |
| 4 | 130 | 92/64 | VPB | 80 | 142/100 | + | 70 | 120/90 | 90 |
| 5 | 140 | 140/100 | vpb or VT | 150 | 170/160 | + | 150 | 165/156 | 60 |
| 6 | 200 | 130/100 | VT | 120 | 120/100 | + | 120 | 120/100 | 120 |
| 7 | 180 | 120/80 | VT | 160 | 60/40 | ± | 120 | 60/40 | 30[##] |
| 8 | 100 | 80/55 | VT | 120 | 120/80 | + | 90 | 120/80 | 40[##*] |
| 9 | 120 | 50/30 | VT | 150 | 100/70 | + | 100 | 100/80 | 180* |

TABLE 1.-continued
EFFECT OF COMPOUND I ON OUABAIN-INDUCED ARRHYTHMIA IN THE CAT After anethesia with 40 mg/kg Nembutal, arrhythmia was induced by the administration of ouabain i.v., either in small doses or by constant infusion, to a total dose of 75–80 µg/kg. Then Compound I was given as a bolus i.v. injection of 1 mg/kg. (Nembutal was given i.p.)

| | Normal | | Arrhythmia | | | Compound I treated | | | |
|---|---|---|---|---|---|---|---|---|---|
| Serial | H.R. | B.P. | Type | H.R. | B.P. | S.R. | H.R. | B.P. | Duration (min) |
| 10 | 170 | 140/90 | VPB | 70 | 90/70 | + | 90 | 90/75 | 120## |

Abbreviations and symbols:
H.R.-heart rate, per min.
B.P.-blood pressure in mm.
VPB-ventricular premature beats.
VT-ventricular tachycardia.
S.R.-sinus rhythm, + denotes return to the rhythm.
Duration-period of observation from onset of reversal of arrhythmia.
-0.5 mg/kg of EO-122 used. ## - Arrhythmia reappeared but was suppressed again with an additional dose of EO-122, 1 mg/kg for 2, 7 and 8 and 0.5 mg/kg for 10.
*-with stimulation of the vagus.

TABLE 2.
EFFECT OF LIDOCAINE ON OUABAIN-INDUCED ARRHYTHMIA IN CATS.

Conditions are the same as those given in Table 1.

| | Normal | | Arrhythmia | | | Lidocaine-treated# | | | |
|---|---|---|---|---|---|---|---|---|---|
| Serial | H.R. | B.P. | Type | H.R. | B.P. | S.R. | H.R. | B.P. | Duration |
| 11 | 180 | 120/80 | VT | 160 | 60/40 | − | 150 | 60/40 | none## |
| 12 | 140 | 85/70 | VPB | 120 | 140/100 | + | 110 | 120/80 | 2 min## |
| 13 | 130 | 92/64 | VPB | 80 | 130/100 | + | 80 | 130/100 | 3 min## |

Abbreviations are same as given in Table 1.
-Lidocaine HCl was given as a single i.v. injection at the rate of 4 mg/kg in 11 and 12 and 1.6 mg/kg in 13.
-Arrhythmia reappeared.

TABLE 3.
EFFECT OF COMPOUND I ON OUABAIN-INDUCED ARRHYTHMIA IN DOGS.

Conditions are those described in Table 1.

| | Normal | | Arrhythmia | | | Compound I treated | | | |
|---|---|---|---|---|---|---|---|---|---|
| Serial | H.R. | B.P. | Type | H.R. | B.P. | S.R. | H.R. | B.P. | Duration |
| 14 | 130 | 125/90 | VT | 180 | 100/80 | + | 170 | 100/80 | 40 min# |
| 15 | 110 | 130/100 | VT | 200 | 140/110 | + | 170 | 140/110 | 25 min# |

Abbreviations are same as given in Table 1.
-Arrhythmia reappeared after this period but was suppressed by one i.v. injection of 0.25 mg/kg EO-122.

The effect of parenteral administration of Compound I on occlusion-induced arrhythmias in conscious dogs was determined. Occulsion was achieved by ligation of the left anteria descending coronary artery on 5 dogs. The animals developed arrhythmia but recovered spontaneously after 3 or 4 days.

Compound I was administered once within 24 hours and once within 48 hours after ligation. Within the 24 hour period, one bolus i.v. injection of 3 mg/kg restored full, uninterrupted sinus rhythm for as long as 20 minutes, followed by mixed stretches of SR, VT and VPB's for 2 to 3 hours. Treatment within the next 24 hours required a lower effective dose, e.g., 1.5 mg/kg, with similar results. Therapeutic blood levels were 5 and 2.5 µg/cc blood, accordingly.

In the same animals, lidocaine was either completely ineffective or of ultra-short duration, when applied as a bolus i.v. injection of 3 mg/kg. The tests with lidocaine were performed either 2 hours before treatment with Compound I or 2 hours following such treatment, with the assumption that the effect is not cumulative at such an interval.

Tests were also carried out to determine the effect of oral administration of Compound I on occlusion induced arrhythmias in conscious dogs.

Arrhythmia was induced by occlusion of the left anterior descending artery, as above described. Following this, Compound I was administered orally to the animals at the rate of 15–20 mg/kg, the dose being divided among 4 to 6 gelatin capsules, without prior treatment such as micronization or admixture with a diluent or carrier. In all cases, the drug was fully effective in the restoration of normal sinus rhythm, but with a delay of 11 to 60 minutes after administration, depending on the severity of the condition.

The pharmacokinetic parameters of Compound I were determined in conscious dogs suffering from occlusion-induced arrhythmia. After intravenous injection of a single therapeutic dose, venous blood samples were withdrawn at given intervals, heparinized and analyzed for their content of Compound I by gas chromatography. The following data were derived:

| | |
|---|---|
| Biological half-life ($t_{\frac{1}{2}}$) | 4 to 5 hours |
| $t_{\frac{1}{2}}$ for distribution | 5 minutes |
| volume of distribution | 0.2 liter/kg body weight |
| Therapeutic body levels | 2.5–5 µg/ml |

The biological availability of Compound I administered by the oral route was determined first in a conscious, healthy dog that received a dose of 7.5 mg/kg subdivided in 6 gelatin capsules that were slipped down its throat. Peak blood concentration was reached within one hour after ingestion and was of the order of 1.5–2 μg/ml blood. Within 4 hours after ingestion, about 80 percent of the ingested dose had been absorbed and could be accounted for by measurement of the AUC (area under curve) of the combined absorption-elimination kinetics. In conscious arrhytnmic dogs, bioavailability of the drug appears to be of the same order.

The following is the summary of the more important properties of Compound I as compared to those of lidocaine:

| Parameter | Compound I | Lidocaine |
|---|---|---|
| Single therapeutic dose for suppression of | | |
| Ouabain-induced arrhythmia | 0.5–1 mg/kg,i.v. | 1–4 mg/kg,i.v. |
| Duration of effect | about 1 hour | about 2 to 4 minutes |
| Onset of effect | about 2 minutes | about 2 minutes |
| Occlusion-induced arrhythmia within | | |
| 1st 24 hr. after operation | 3 mg/kg,i.v. | often ineffective |
| Duration of effect | 20 min to 2 hr. | 1 to 2 when effective |
| Onset of effect | 2 minutes | 2 minutes |
| Within 2nd 24 hr. after operation | 1.5 mg/kg,i.v. | 1 to 3 mg/kg,i.v. |
| Duration of effect | 1 to 4 hr. | 1 to 3 min. |
| Therapeutic blood levels | 2.5–5 μg/ml | 2.5–5 μg/ml |
| Bioavailability by oral route | about 80% | insignificant |
| Single therapeutic oral dose for suppression of occlusion-induced arrhythmia | 15–20 mg/kg | not applicable |
| Side effects | | |
| Hypotension | none | about 20% |
| Emesis | partial | partial |
| CNS-effects | none | extensive |
| $t_{\frac{1}{2}}$ for distribution | 5 min | 5 min |
| $t_{\frac{1}{2}}$ for elimination | 4 to 5 hr. | 75–120 min. |
| volume of distribution | 0.2 l/kg | 0.2 l/kg |

It is thus clear that while Compound I of the present invention possesses the antiarrhythmic properties of lidocaine it possesses numerous pharmacological advantages, namely a longer biological half-life, obviating the need of drug administration by constant infusion; excellent bioavailability after oral administration, obviating the need of multiple injections; and absence of side effects such as hypotension and CNS stimulation. Furthermore, it appears that compound I is not significantly degraded by the liver. It is thus clear that in accordance with the present invention Compound I and the free base and other pharmacologically effective acid addition salts thereof can be used in single or multiple intravenous dose for the management of arrhythmias after acute myocardial infarction, can be used in emergencies before and during the transfer of a patient to an intensive care unit; can be used for the management of arrhythmias due to digitalis intoxication and also can be used orally for continued management.

As indicated above, these effects are achieved only with the compound which is the 2,6-xylidide of quinuclidine-3-carboxylic acid and the physiologically compatible acid addition salts thereof, while the isomer thereof, namely the 2,6-xylidide of quinuclidine-2-carboxylic acid is both neurotoxic and devoid of useful antiarrhythmic properties. This is confirmed by the tests of compound II, namely the hydrochloride of 2,6-xylidide of quinuclidine-2-carboxylic acid, which was produced both by the method of French Pat. No. 1,566,045, and by the method of the present invention. Administration of Compound II to albino mice by the intraperitoneal route induced the following symptoms:

| Dose range | Effects |
|---|---|
| 20–30 mg per kg | increased locomotion, excitation |
| 40–60 mg per kg | pronounced neurotoxicity, ataxia, partial paralysis |
| 100 mg. per kg | lethal dose. Cause of death seems to be due to respiratory failure. |

EFFECT OF COMPOUND II IN DRUG-INDUCED ARRHYTHMIA

Arrhythmia was induced in 2.7 kg cat, previously anesthetized with nembutal, by the slow infusion of ouabain over a period of one hour and to a total dose of 70 μg per kg. At this stage, the electrocardiogram showed clear signs of arrhythmia, mainly ventricular premature beats and ventricular tachycardia. An intravenous injection of Compound II at the rate of 1.1 mg per kg precipitated ventricular fibrillation and death.

EFFECT OF COMPOUND II IN ARRHYTHMIA INDUCED BY CORONARY OCCLUSION

Arrhythmia was induced in a dog of 15 kg body weight, by ligation of the left anteria descending coronary artery with a silk thread number 000. Twenty-four hours after surgery, the electrocardiogram showed clear signs of arrhythmia, mainly ventricular tachycardia. An intravenous injection of Compound II at the rate of 3 mg per kg produced only a fleeting response in the electrocardiogram with only a few signs of improvement. On the other hand, the animals exhibited clear signs of neurotoxicity such as undue excitement and lateral movements of the head.

It is thus clear that Compound II cannot be used as a cardiac antiarrhythmic agent.

While the method of the present invention has been illustrated in particular with the production of Compounds I and II, it is apparent that this is a general method of producing these and similar compounds according to which a quinuclidine carboxylic acid of the formula:

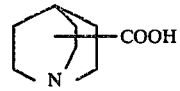

is reacted in anhydrous chloroform in the presence of oxalo chloride with an aniline of the formula:

wherein $R_1$ and $R_2$ have the same definitions as above, to produce the corresponding quinuclidine carboxylic acid xylidide which can then be recovered.

What is claimed is:

1. Method of treating cardiac arrhythmia, which comprises administering to a patient requiring cardiac antiarrhythmic treatment a cardiac antiarrhythmic effective amount of a compound selected from the group consisting of the 2-6-xylidide quinuclidine-3-carboxylic acid and pharmaceutically acceptable acid addition salts thereof.

2. Method according to claim 1 wherein the compound administered is a pharmaceutically acceptable salt of the 2-6-xylidide of quinuclidine-3-carboxylic acid.

3. Method according to claim 2 wherein said salt is the hydrochloride.

4. Method according to claim 1 wherein the administration is by injection.

5. Method according to claim 1 wherein the administration is oral.